(12) United States Patent
Graumann et al.

(10) Patent No.: US 9,524,547 B2
(45) Date of Patent: Dec. 20, 2016

(54) METHOD FOR ARTIFACT-FREE RENDERING OF METAL PARTS IN THREE-DIMENSIONALLY RECONSTRUCTED IMAGES

(71) Applicant: SIEMENS AKTIENGESELLSCHAFT, Munich (DE)

(72) Inventors: Rainer Graumann, Hoechstadt (DE); Gerhard Kleinszig, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 192 days.

(21) Appl. No.: 14/215,295

(22) Filed: Mar. 17, 2014

(65) Prior Publication Data
US 2014/0267255 A1    Sep. 18, 2014

(30) Foreign Application Priority Data
Mar. 15, 2013 (DE) .......... 10 2013 204 552

(51) Int. Cl.
*G06T 7/00* (2006.01)
*G06T 15/00* (2011.01)
*G06T 19/00* (2011.01)
*A61B 6/03* (2006.01)
(Continued)

(52) U.S. Cl.
CPC .......... *G06T 7/0012* (2013.01); *A61B 6/032* (2013.01); *A61B 6/4441* (2013.01);
(Continued)

(58) Field of Classification Search
CPC .................................................. G06T 15/00
(Continued)

(56) References Cited

U.S. PATENT DOCUMENTS 6,747,646 B2 * 6/2004 Gueziec et al. ............... 345/426
7,117,027 B2 * 10/2006 Zheng et al. .................. 600/426
(Continued)

FOREIGN PATENT DOCUMENTS

| DE | 102010020284 A1 | 11/2011 |
| DE | 102011075912 A1 | 11/2012 |
| DE | 102011083063 A1 | 3/2013 |

OTHER PUBLICATIONS

Kakkar Rahul et al., "Posterior lumbar interbody fusion and segmental lumbar lordosis", Eur J Orthop Surg Taumatol (2007), vol. 17, pp. 125-129.

*Primary Examiner* — Kimbinh T Nguyen
(74) *Attorney, Agent, or Firm* — Laurence Greenberg; Werner Stemer; Ralph Locher

(57) ABSTRACT

A method for artifact-free rendering of metal parts in 3D three-dimensionally reconstructed images of an examination object in a patient, includes recording a 3D scan without metal parts producing a 3D data record, recording n projection images with metal parts from known locations or directions, 2D/3D registering bone in the n projection images with the 3D data record, 2D/3D registering of the metal parts from the n projection images and 3D models of the metal parts, calculating locations of the metal parts in the 3D data record based on the 2D/3D registration thereof, and superposing all current locations of the metal parts in the 3D data record. There is no need for a new 3D scan to check current screw positions. The 3D representation of screw positions in the bone is performed without artifacts, enabling reliable assessment of screw locations, for example in spinal column surgery.

7 Claims, 3 Drawing Sheets

(51) Int. Cl.
  *A61B 6/00* (2006.01)
  *G06T 11/00* (2006.01)
(52) U.S. Cl.
  CPC ............ *A61B 6/4458* (2013.01); *A61B 6/487* (2013.01); *A61B 6/488* (2013.01); *A61B 6/504* (2013.01); *A61B 6/5205* (2013.01); *A61B 6/5258* (2013.01); *G06T 7/004* (2013.01); *G06T 7/0024* (2013.01); *G06T 11/008* (2013.01); *G06T 15/00* (2013.01); *G06T 19/00* (2013.01); *G06T 2207/10072* (2013.01); *G06T 2207/10121* (2013.01); *G06T 2207/30052* (2013.01)
(58) Field of Classification Search
  USPC ....... 345/420, 426, 424, 629, 419, 634, 639; 600/407, 425; 378/207, 42; 382/285, 294, 382/132; 715/532; 128/922; 700/245; 606/130; 623/908; 706/924
  See application file for complete search history.

(56) References Cited

U.S. PATENT DOCUMENTS

| | | | |
|---|---|---|---|
| 7,369,695 B2* | 5/2008 | Zettel | A61B 6/032 378/4 |
| 7,457,443 B2* | 11/2008 | Persky | 382/128 |
| 7,500,784 B2 | 3/2009 | Grebner et al. | |
| 8,023,767 B1* | 9/2011 | Ning | A61B 6/032 382/128 |
| 8,229,246 B2* | 7/2012 | Ning | A61B 6/032 382/128 |
| 8,891,847 B2* | 11/2014 | Helm | G06T 11/00 382/131 |
| 9,177,374 B2* | 11/2015 | Stayman | G06T 7/0012 |
| 9,317,661 B2* | 4/2016 | Helm | G06T 19/20 |
| 2004/0087852 A1* | 5/2004 | Chen et al. | 600/407 |
| 2006/0251313 A1* | 11/2006 | Lievin | G06T 11/005 382/131 |
| 2008/0021310 A1* | 1/2008 | Amiot et al. | 600/425 |
| 2008/0119712 A1* | 5/2008 | Lloyd | 600/407 |
| 2008/0154120 A1* | 6/2008 | von Jako et al. | 600/411 |
| 2011/0282189 A1 | 11/2011 | Graumann | |
| 2012/0008845 A1* | 1/2012 | Ning | A61B 6/032 382/131 |
| 2013/0188848 A1* | 7/2013 | Helm | G06T 11/00 382/131 |
| 2014/0010431 A1* | 1/2014 | Stayman | G06T 7/0012 382/131 |
| 2014/0121676 A1* | 5/2014 | Kostrzewski et al. | 606/130 |
| 2015/0078647 A1* | 3/2015 | Helm | G06T 11/00 382/132 |

* cited by examiner

METHOD FOR ARTIFACT-FREE RENDERING OF METAL PARTS IN THREE-DIMENSIONALLY RECONSTRUCTED IMAGES

CROSS-REFERENCE TO RELATED APPLICATION

This application claims the priority, under 35 U.S.C. §119, of German Patent Application DE 10 2013 204 552.2, filed Mar. 15, 2013; the prior application is herewith incorporated by reference in its entirety.

BACKGROUND OF THE INVENTION

Field of the Invention

The invention relates to a method for artifact-free rendering of metal parts in three-dimensionally reconstructed images of an examination object in a patient. With the aid of such a method it is possible to check screw locations, for example in spinal column surgery.

An angiography system for carrying out such a rendering method is known e.g. from U.S. Pat. No. 7,500,784 B2, which will be explained below on the basis of FIG. 1.

FIG. 1 shows a monoplanar x-ray system, depicted as an example, with a C-arm 2 held by a stand 1 in the form of a six-axis industrial or folding-arm robot, attached to the end of which there are an x-ray radiation source, for example an x-ray emitter 3 with x-ray tubes and a collimator, and an x-ray image detector 4 as an image recording unit.

The folding-arm robot, which is, for example, known from U.S. Pat. No. 7,500,784 B2, preferably has six axes of rotation and therefore six degrees of freedom. By using the folding-arm robot, it is possible to adjust the C-arm 2 in space as required, for example by virtue of it being rotated about a center of rotation between the x-ray emitter 3 and the x-ray image detector 4. The angiographic x-ray system 1 to 4 according to the invention is rotatable, in particular, about centers of rotation and axes of rotation in the C-arm plane of the x-ray image detector 4, preferably about the center point of the x-ray image detector 4 and about the center point of the axes of rotation intersecting the x-ray image detector 4.

The known folding-arm robot has a main frame, which is securely attached e.g. to a floor. A carousel is affixed thereto in a manner rotatable about a first axis of rotation. A robot rocker is attached pivotably about a second axis of rotation on the carousel, on which a robot arm is attached rotatably about a third axis of rotation. A robot hand is attached rotatably about a fourth axis of rotation at the end of the robot arm. The robot hand has an attachment element for the C-arm 2, which can be pivoted about a fifth axis of rotation and can be rotated about a sixth axis of rotation extending perpendicular thereto.

The realization of the x-ray diagnostics apparatus is not dependent on the industrial robot. It is also possible to make use of conventional C-arm devices.

The x-ray imaging detector 4 can be a rectangular or quadratic, flat semiconductor detector which is preferably made from amorphous silicon (a-Si). However, it is also possible to use integrating and possibly counting CMOS detectors.

A patient 6 to be examined as an examination object is situated on a slab 5 of a patient mounting table in the beam path of the x-ray emitter 3. Attached to the x-ray diagnostics apparatus is a system control unit 7 with an image system 8, which receives and processes image signals from the x-ray image detector 4 (operating elements, for example, have not been depicted). The x-ray images then can be inspected on displays of a monitor suspension 9. A known device 10, the function of which will still be described in more detail, is furthermore provided in the system control unit 7.

As depicted in FIG. 2 in a simplified manner, the angiographic x-ray system also can have a normal ceiling-mounted or floor-mounted holder for the C-arm 2, in place of the x-ray system with the stand 1 in the form of the six-axis industrial or folding-arm robot depicted in FIG. 1 in an exemplary manner.

In place of the C-arm 2, which is depicted in an exemplary manner, the angiographic x-ray system also can have separate ceiling-mounted and/or floor-mounted holders for the x-ray emitter 3 and the x-ray image detector 4 which, for example, are coupled in an electronically rigid manner.

The x-ray emitter 3 emits a beam 11 emanating from a beam focus of the x-ray radiation source thereof and impinging on the x-ray image detector 4. If 3D data records are to be created according to the so-called DynaCT method (a method for rotational angiography), the rotatably mounted C-arm 2 with the x-ray emitter 3 and the x-ray image detector 4 is rotated in such a way that, as shown schematically in FIG. 2 in a top view onto the axis of rotation, the x-ray emitter 3, illustrated therein figuratively by the beam focus thereof, and the x-ray image detector 4 move along an orbit 13 around an object 12 to be examined, which is situated in the beam path of the x-ray emitter 3. It is possible to pass over the orbit 13 completely or in part for the purposes of producing a 3D data record.

In this case, according to the DynaCT method, the C-arm 2 with the x-ray emitter 3 and the x-ray image detector 4 preferably moves over at least an angular range of 180°, for example 180° plus a fan angle, and records projection images from different projections in quick succession. The reconstruction can be performed while using only a portion of this recorded data.

By way of example, the object 12 to be examined can be an animal or human body, as well as a body phantom.

The x-ray emitter 3 and the x-ray image detector 4 each move around the object 12 in such a way that the x-ray emitter 3 and the x-ray image detector 4 lie opposite one another on opposite sides of the object 12.

In the case of normal radiography or fluoroscopy carried out by using such an x-ray diagnostics apparatus, medical 2D data from the x-ray image detector 4 are optionally buffer stored in the image system 8 and subsequently rendered on the monitor 9.

However, despite the application of metal artifact corrections, displaying metallic objects such as e.g. implants or screws, is still difficult in the 3D reconstructed images as a result of the occurrence of artifacts. By way of example, those artifacts can lead to misinterpretations of the screw positions, for example in the case of fusion operations on the spinal column. Such a fusion operation may be the posterior lumbar inter vertebral fusion (PLIF), a surgical technique for fusing lumbar vertebrae by removing the inter vertebral disk and replacing it by a titanium basket, wherein the vertebra is subsequently still internally stabilized by fixation, as can be gathered from e.g. the article "Posterior Lumbar Inter Body Fusion And Segmental Lumbar Lordosis" by Rahul Kakkar, et al., published in Eur J Orthop Surg Traumatol (2007), vol. 17, pages 125-129.

These days, the following methods find use for reducing the problem of the metal artifacts:
   metal artifact correction,
   3D scanning in the ideal rotational orientation (for minimizing the artifacts) and/or experience-based evaluation of the artifact-afflicted images.

German Patent Application DE 10 2011 083 063.4 proposes a method for producing planning data correlated to a placement of an implant at an operating site in a patient, in which 3D image data and, using an imaging system, 2D image data of the operation site are produced. The 3D image data are assigned, at the correct location, to a coordinate system of the imaging system using the 2D image data, a 3D model of the implant is adapted virtually into the 3D image data at the operating site and the planning data are produced in the coordinate system of the imaging system using the 3D image data containing the 3D model.

SUMMARY OF THE INVENTION

It is accordingly an object of the invention to provide a method for artifact-free rendering of metal parts in three-dimensionally reconstructed images, which overcomes the hereinafore-mentioned disadvantages of the heretofore-known methods of this general type and does so without problems in three-dimensionally reconstructed images of an examination object in a patient.

With the foregoing and other objects in view there is provided, in accordance with the invention, a method for artifact-free three-dimensional rendering of metal parts, comprising the following steps:
  S1) recording a 3D scan without metal parts for producing a 3D data record,
  S2) recording n projection images with metal parts from known locations or directions,
  S3) 2D/3D registering of the bone in the n projection images with the 3D data record,
  S4) 2D/3D registering of the metal parts from the n projection images and the 3D models of the metal parts,
  S5) calculating the locations of the metal parts in the 3D data record on the basis of the 2D/3D registration thereof, and
  S6) superposing all current locations of the metal parts into the 3D data record.

As a result, no new 3D scan is required to check the current screw positions. The 3D representation of the screw positions in the bones is carried out without artifacts. This enables a reliable assessment of the screw locations, for example in spinal column surgery.

In accordance with another advantageous mode of the invention, the recording of the 3D scan without metal parts can be a presurgical CT scan, a presurgical MRI scan or an intrasurgical C-arm scan.

In accordance with a further mode of the invention, the 3D data record is produced presurgery and the n projection images are produced during surgery.

In accordance with an added advantageous mode of the invention, the number n of projection images is a value from two to ten, in particular a value from four to six.

In accordance with an additional mode of the invention, the metal parts can be screws, in particular pedicle screws.

In accordance with a concomitant advantageous mode of the invention, the superposition of all current locations of the metal parts according to method step S6) can be brought about by superposition (alignment), in the correct position, of the 3D models.

Other features which are considered as characteristic for the invention are set forth in the appended claims.

Although the invention is illustrated and described herein as embodied in a method for artifact-free rendering of metal parts in three-dimensionally reconstructed images, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
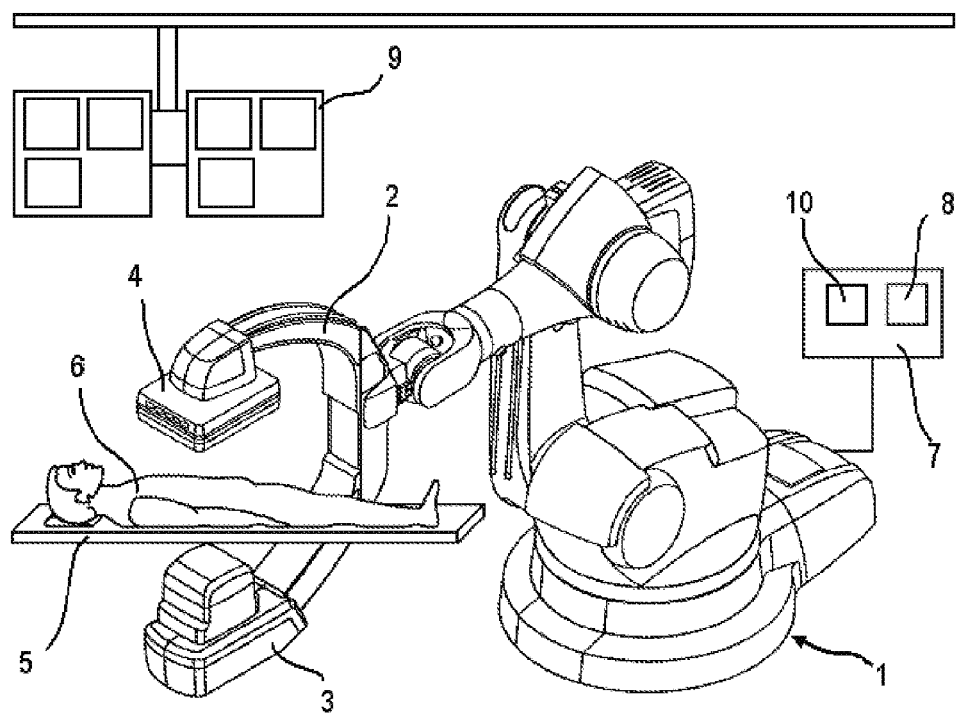
FIG. 1 is a diagrammatic, perspective view of a known C-arm angiography system using an industrial robot as a support device.
Figure 2:
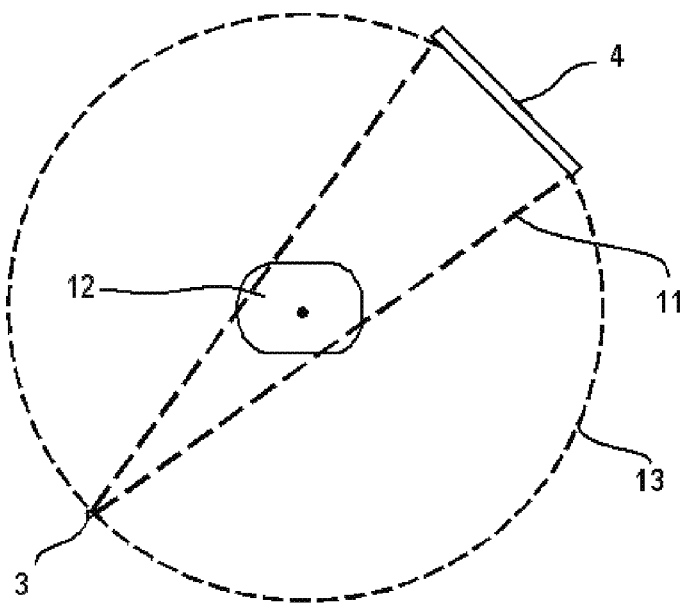
FIG. 2 is a diagram showing geometrical relationships during rotation angiography using the C-arm angiography system according to FIG. 1.
Figure 3:
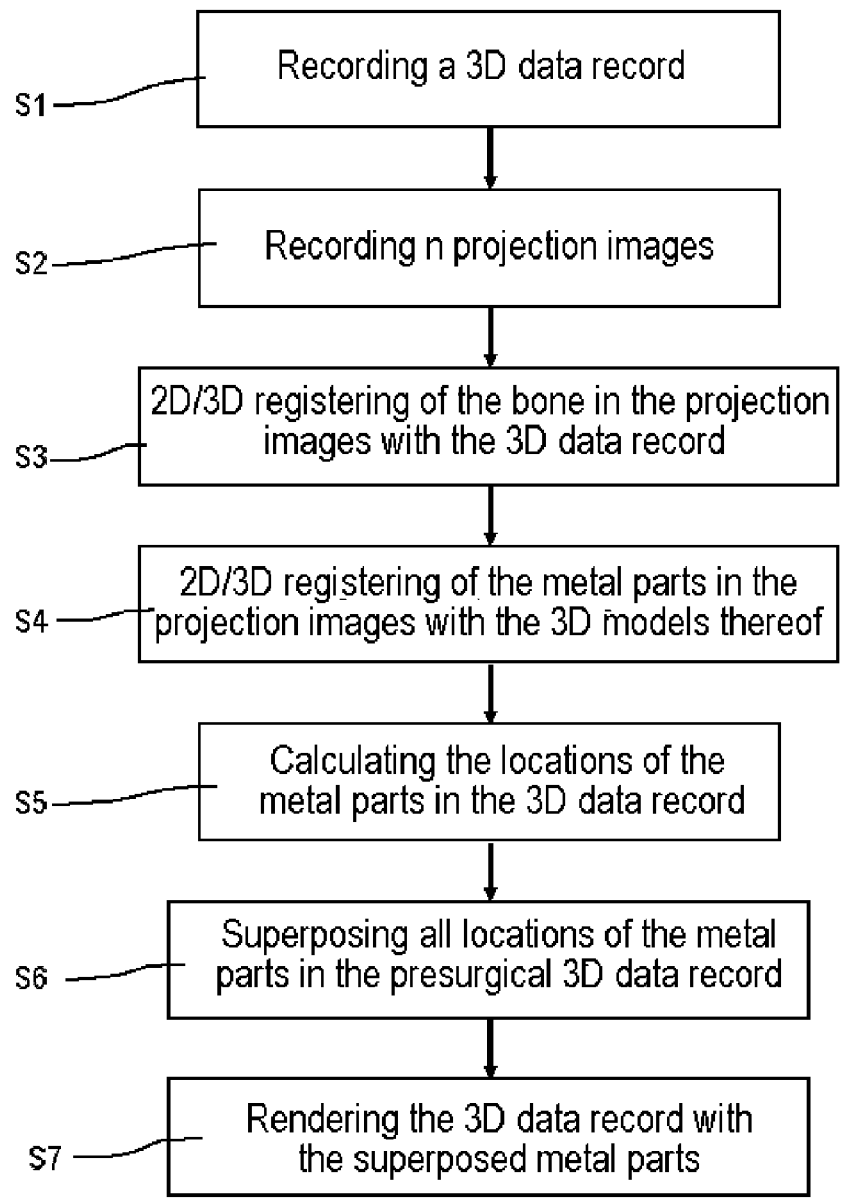
FIG. 3 is a flow diagram showing a procedure according to the invention for rendering 3D images.

Referring now to the figures of the drawings in detail and first, particularly, to FIG. 3 thereof, there is seen a procedure according to the invention for rendering 3D images, in which a 3D scan without metal parts is recorded in a first method step S1) for producing a 3D data record. The recording of the 3D scan without metal parts can be a presurgical CT scan, a presurgical MRI scan or an intrasurgical C-arm scan carried out by using rotational angiography using the C-arm angiography system according to FIG. 1.

After the introduction of the metal parts, for example pedicle screws, a few projection images with these pedicle screws are recorded from known locations or directions by using the C-arm angiography system in accordance with a second method step S2).

In a third method step S3), there is 2D/3D registering of the bone in the projection images with the 3D data record.

Subsequently, the n projection images and the 3D models of the metal parts are registered in a 2D/3D registration of the metal parts as a fourth method step S4).

Due to a subsequent location calculation of the metal parts in the 3D data record as a fifth method step S5), there is a superposition of all current locations of the metal parts in the 3D data record as a method step S6). Rendering the 3D data record with the superposed metal parts is indicated as a method step S7).

Figure 4:
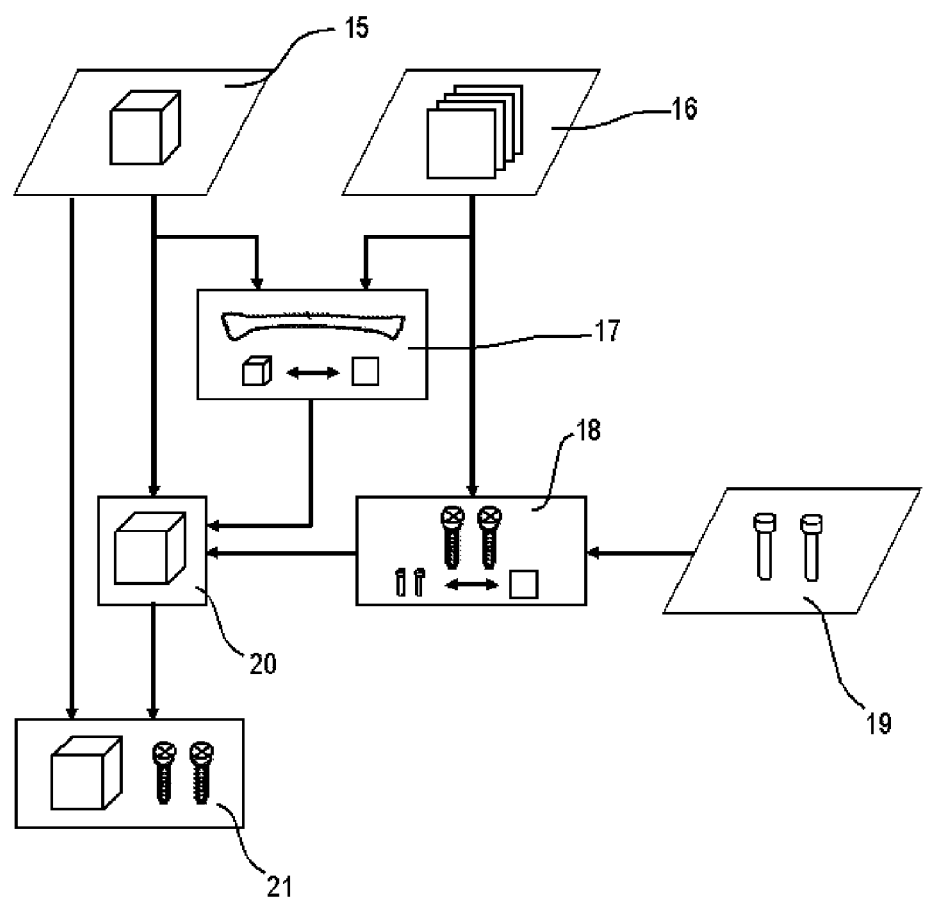
FIG. 4 is a flowchart of the procedure according to FIG. 3.

FIG. 4 shows a flowchart for rendering 3D images, in which a presurgical or intrasurgical 3D data record 15 without metal parts and a few (e.g. n) projection images 16 with these metal parts are subjected to a 2D/3D registration 17 of the bone in the projection images 16 with the 3D data record 15. The presurgical or intrasurgical 3D data record 15 can originate from a 3D scan, which was recorded by using rotation angiography with the aid of a computed tomography scanner or a C-arm angiography system. The n projection images, which were produced from known locations or directions after the introduction of e.g. the pedicle screws and which include these pedicle screws, are recorded by using the C-arm angiography system.

There subsequently is a 2D/3D registration 18 of the metal parts from the n projection images 16 with 3D models 19 of the metal parts. Thereafter, there is a location calculation 20 of the metal parts in the 3D data record 15, on the basis of which emerges a superposition 21 of all current locations of the metal parts in the 3D data record 15.

According to the invention, the following method steps are proposed for solving the problem of metal artifacts:
1. recording a 3D scan 15 without screws by using a presurgical CT scan, or an intrasurgical 3D-C-arm scan,
2. recording a few projection images 16, for example four to six, from known locations after the introduction of screws,
3. 2D/3D registering 17 of the bone with the 3D data record 15,
4. 2D/3D registering 18 of the screws from the projection images 16 and the 3D models 19 of the screws, and
5. calculating 20 the screw locations in the 3D data record 15 and superposing 21 all current screw positions in the 3D data record.

The method works best if the part of the bone in which the screws are placed need not be set, as is the case e.g. when introducing pedicle screws into a vertebra, e.g. in PLIF, in prosthetics or when attaching screws in non-fractured (partial) bone regions.

As a result of this, no 3D scan is required to check the current bone positions. Therefore, the 3D illustration of the screw positions in the bone is without artifacts. This enables a reliable assessment of the screw locations.

The invention claimed is:

1. A method for artifact-free rendering of metal parts in three-dimensionally reconstructed images of an examination object in a patient, the method comprising the following steps:
   S1) recording a 3D scan without metal parts for producing a 3D data record;
   S2) recording a number n of projection images with metal parts from different known locations or directions, the number n of projection images being selected as a value from two to ten;
   S3) 2D/3D registering of bone in the n projection images with the 3D data record;
   S4) 2D/3D registering 3D models of the metal parts to metal parts in the n projection images;
   S5) calculating locations of the metal parts in the 3D data record on the basis of the 2D/3D registration thereof; and
   S6) superposing all current locations of the metal parts in the 3D data record.

2. The method according to claim 1, which further comprises carrying out the recording of the 3D scan without metal parts as a presurgical computed tomography (CT) scan, a presurgical magnetic resonance imaging (MRI) scan or an intrasurgical C-arm scan.

3. The method according to claim 1, which further comprises producing the 3D data record presurgery and producing the n projection images during surgery.

4. The method according to claim 1, wherein the metal parts are screws.

5. The method according to claim 1, wherein the metal parts are pedicle screws.

6. The method according to claim 1, which further comprises bringing about the superposition of all current locations of the metal parts according to method step S6) by superposition of the 3D models.

7. A method for artifact-free rendering of metal parts in three-dimensionally reconstructed images of an examination object in a patient, the method comprising the following steps:
   S1) recording a 3D scan without metal parts for producing a 3D data record;
   S2) recording a number n of projection images with metal parts from different known locations or directions, the number n of projection images being selected as a value of from four to six;
   S3) 2D/3D registering of bone in the n projection images with the 3D data record;
   S4) 2D/3D registering 3D models of the metal parts to metal parts in the n projection images;
   S5) calculating locations of the metal parts in the 3D data record on the basis of the 2D/3D registration thereof; and
   S6) superposing all current locations of the metal parts in the 3D data record.

* * * * *